Figure 1:
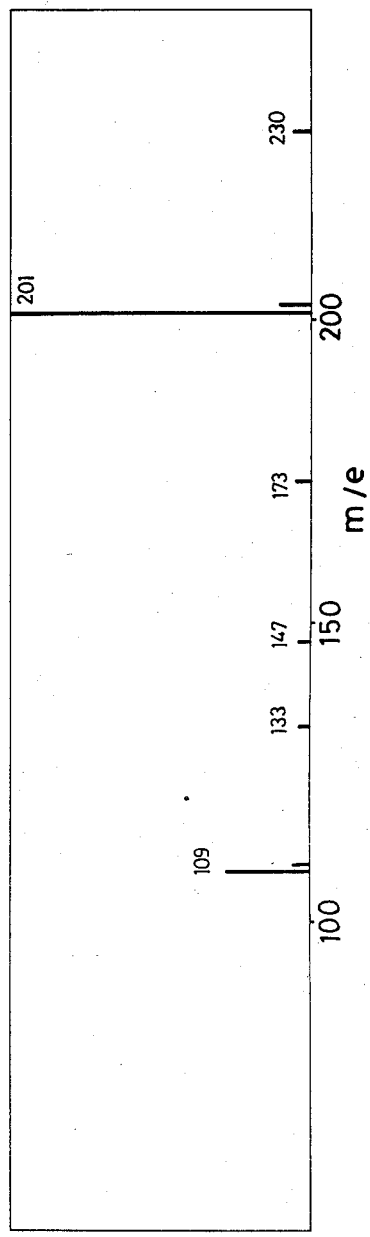

United States Patent [19]

Kobayashi et al.

[11] Patent Number: 4,567,293

[45] Date of Patent: Jan. 28, 1986

[54] 2-[PARA-(2-SUBSTITUTED OR UNSUBSTITUTED-3,3,3-TRI-FLUORO-PROPYL)PHENYL]PROPIONIC ACID OR A SALT THEREOF

[75] Inventors: Yoshiro Kobayashi, Tokyo; Itsumaro Kumadaki, Hachiohji; Takashi Yamauchi; Akira Iizuka, both of Iwaki, all of Japan

[73] Assignee: Kureha Kagaku Kogyo Kabushiki Kaisha, Tokyo, Japan

[21] Appl. No.: 702,861

[22] Filed: Feb. 20, 1985

Related U.S. Application Data

[63] Continuation of Ser. No. 430,779, Sep. 30, 1982, abandoned.

[30] Foreign Application Priority Data

Oct. 14, 1981 [JP] Japan ................................ 56-163872
Jan. 14, 1982 [JP] Japan .................................... 57-4747
Aug. 6, 1982 [JP] Japan ................................ 57-136937

[51] Int. Cl.$^4$ ..................... C07C 57/30; C07C 53/134

[52] U.S. Cl. ..................................... 562/496; 560/105; 514/570; 514/532

[58] Field of Search ........................ 562/496; 560/105; 514/570, 532

[56] References Cited

U.S. PATENT DOCUMENTS

3,385,886  5/1968  Nicholson ........................... 562/496
4,131,747 12/1976 Kurono et al. ...................... 562/491

FOREIGN PATENT DOCUMENTS

2100632  5/1971  France .
6026429  8/1976  Japan ................................. 562/496
1095035  8/1976  Japan ................................. 562/496
6138140 10/1981  Japan ................................. 562/496

*Primary Examiner*—Paul J. Killos

[57] ABSTRACT

A novel compound of 2-[para-(2-substituted or unsubstituted-3,3,3-trifluoropropyl)phenyl]propionic acid or a salt thereof which has a specific pharmacological activity and a pharmaceutical composition comprising the novel compound as an active ingredient are disclosed.

12 Claims, 13 Drawing Figures

2-[PARA-(2-SUBSTITUTED OR UNSUBSTITUTED-3,3,3-TRI-FLUOROPROPYL)-PHENYL]PROPIONIC ACID OR A SALT THEREOF

This application is a continuation of Ser. No. 430,779, filed Sept. 30, 1982, now abandoned.

This invention relates to novel compounds and their use as anti-inflammatory medicine. More particularly, this invention relates to novel compounds of 2-[para-(2-substituted or unsubstituted-3,3,3-trifluoropropyl)-phenyl]propionic acid or a salt thereof which are useful as anti-inflammatory medicines.

It is an object of this invention to provide a novel compound of 2-[para-(2-substituted or unsubstituted-3,3,3-trifluoropropyl)phenyl]propinonc acid or a salt thereof. Furthermore, still another object is to provide a medicine comprising the novel compound.

The novel compounds according to this invention (hereinafter referred to as the present compound) are 2-[para-(2-substituted or unsubstituted-3,3,3-trifluoropropyl)phenyl]propionic acid represented by the following formula:

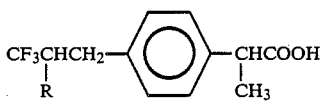

wherein R is a hydrogen atom, a methyl group or a trifluoromethyl group.

The present compound includes salt thereof. The salt is an alkali or alkaline earth metal salt such as sodium salt, potassium salt, calcium salt, magnesium salt, etc., aluminum salt or ammonium salt, preferably sodium or potassium salt.

The present compound can be synthesized according to any of the known various processes. One of the processes is exemplified as follows.

A 2-substituted or unsubstituted-3,3,3-trifluoropropylbenzene is brought into reaction with propionyl chloride in carbon disulfide under the presence of anhydrous aluminum chloride to obtain p-(2-substituted or unsubstituted-3,3,3-trifluoropropyl)propiophenone (hereinafter referred to as the intermediate compound) and then the intermediate compound reacts with methanol in the presence of thallium(III) nitrate followed by hydrolysis to obtain the present compound.

The reaction formulae are shown below.

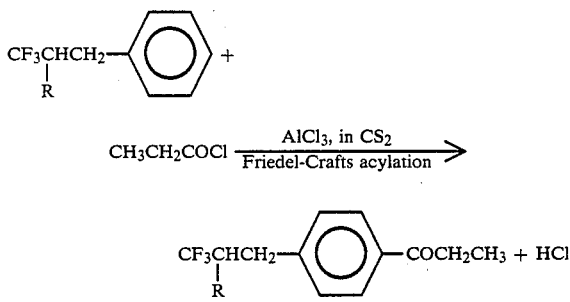

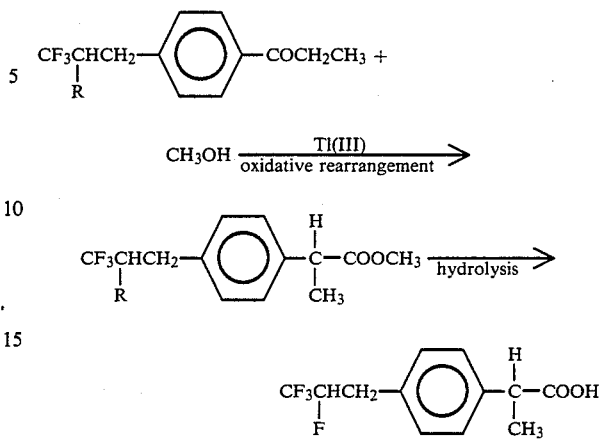

The present compound of salt form is prepared by the conventional method for neutralization by using a base such as hydroxide, carbonate or bicarbonate of an alkali or alkaline earth metal, for example, sodium, potassium, calcium or magnesium, etc., aluminum or ammonium salt.

As seen from Examples described below, the present compound shows an excellent anti-inflammatory activity and a low toxicity. Accordingly, the present compound is useful as a medicine for treating various inflammations.

When the present compound is used for a medicine, the salt must be pharmaceutically acceptable.

The present compound can be used in a dosage unit form such as a drug or a pharmaceutical composition. The content of the present compound in the pharmaceutical composition may be adequately varied, however, it is 0.01 to 100% by weight, preferably 0.1 to 80% by weight of the composition.

The present compound can be perorally or rectally in the various dosage form as a composition together with other drug, and/or a pharmaceutically acceptable diluent, carrier, adjuvant. The dosage form for oral administration may be tablet, sugar-coated tablet, sublingual tablet, capsule, powder, granule, pill, ampoule or the like. The composition may be in the form of pharmaceutically acceptable emulsion, solution, suspension and the like.

The drug or phamaceutical composition of the invention is administered into a human or animal parenterally (for example, rectally) or perorally (including sublingual).

A dose of the drug or pharmaceutical composition of the invention is 0.1 to 200 mg, preferably 1 to 100 mg per day per one kilogram of the body weight in the case of peroral administration into a human, divided into one to four times. However, the dose depends on age, individually, condition of a disease etc. of a human or animal and the dose out of the above-mentioned range may be used.

The invention is illustrated in more detail in the Examples which are not considered as limiting. It is apparent that many modifications and variations of the present invention may be made without departing from the spirit and the scope thereof.

SYNTHESIS OF THE PRESENT COMPOUNDS

EXAMPLE 1

Synthesis of 2-[p-(2-trifluoromethyl-3,3,3-trifluoropropyl)phenyl]-propionic acid 1—1: Synthesis of the intermediate compound Into a 500 ml-three necked, round bottomed flask provided with a mechanical stirrer and a dropping funnel, 100 ml of carbon disulfide was introduced and while stirring, 32.0 g (0.24 mol) of anhydrous aluminum chloride was added to be dispersed in carbon disulfide. A solution of 22.2 g (0.24 mol) of propionyl chloride dissolved in 20 ml of carbon disulfide was dropped into the flask for 15 minutes and then, while keeping the inner temperature at 0° to 5° C., a solution of 48.4 g (0.20 mol) of 3,3,3-trifluoro-2-trifluoromethylpropyl-benzene dissolved in 50 ml of carbon disulfide was added into the flask drop by drop during 2 hours. After 7 hours of stirring from the completion of the addition, the content of the flask was poured into a dilute hydrochloric acid in which ice blocks were floated. After separating the layer of carbon disulfide, it was extracted with ether. The extract was washed with water, dried on calcium chloride and subjected to distillation to remove carbon disulfide to obtain 59 g of the reaction mixture as a pale yellow liquid. On distilling the mixture under a reduced pressure, there was obtained 42 g of the fraction boiling at 135° to 138° under a reduced pressure of 5 mmHg. By analyzing the fraction by gas chromatography, mass spectroscopy, $^1$H-NMR spectroscopy and infrared absorption spectroscopy, it was confirmed that the fraction was an isometric mixture of (2tri-fluoromethyl-3,3,3-trifluoropropyl)propiophenone containing 90% by weight of the para isomer (the intermediate compound).

1-2: Synthesis of the present compound 1-2-1 Preparation of thallium reagent

In a 500 ml-round bottomed flask, 106 g (1.0 mol) of methyl orthoformate and 80 g (2.5 mol) of methanol were mixed at room temperature, and 48.9 g (0.11 mol) of thallium nitrate trihydrate, Tl (NO$_3$)$_3$·3H$_2$O was dissolved in the mixture. Further, 100 g of silica gel was added to the thus formed solution. After stirring the solution for 20 minutes, the solvent was distilled off from the solution, and the residue was dried at 40° C. under a reduced pressure of 10 mmHg for 2 hours to obtain 161 g of white powder as the thallium reagent.

1-2-2 Oxidative rearrangement

In a 1 liter-round bottomed flask provided with a mechanical stirrer and a reflux condenser, 161 g of the thus prepared thallium reagent, 750 ml of carbon tetrachloride and 29.8 g (0.1 mol) of the intermediate compound synthesized in 1-1 were introduced to bring into reaction under reflux condenser for 8 hours. After the reaction was over, the solid material in the reaction mixture was removed by filtration and the solvent was distilled off from the filtrate to obtain 42 g of a yellow liquid.

After dissolving the liquid in 150 ml of ether, it was washed with water, an aqueous 5% solution of sodium hydrogen carbonate and then water, and subjected to disillation to remove ether to obtain 30.8 g of a yellow transparent liquid. On distilling the yellow liquid, 18.1 g of a fraction boiling at 76° to 78° C. under a reduced pressure of 3 mmHg was obtained.

1-2-3 Hydrolysis

Into 18.1 g of the fraction obtained in 1-2-2, 150 ml of ethanol and 4.4 g of sodium hydroxide were added, and the mixture was heated under a reflux condenser for 2 hours. After the reaction was over, the solvent was distilled off from the reaction mixture, and the residue was mixed with 150 ml of water, and then the mixture was washed 2 times with each 150 ml of ether. On adding a dilute hydrochloric acid to the aqueous phase to acidify, an oily precipitate appeared in the aqueous phase. After extracting the preceipitate with ether, the ether was distilled off to obtain 10 g of a reddish brown liquid.

The liquid was further purified by silica gel chromatography while using benzene as a developping solvent to obtain 6.7 g of a pale yellow oily substance, which was then dissolved in 70 ml of n-hexane. On leaving the solution as it is in a refrigerator, crystals separated from the solution were collected and dried to obtain 2.6 g of the purified crystals, which were identified as 2-[p-(2-trifluoromethyl-3,3,3-trifluoropropyl)phenyl]propionic acid by the following analysis.

(1) Melting point; 65°–66° C.

Figure 11:
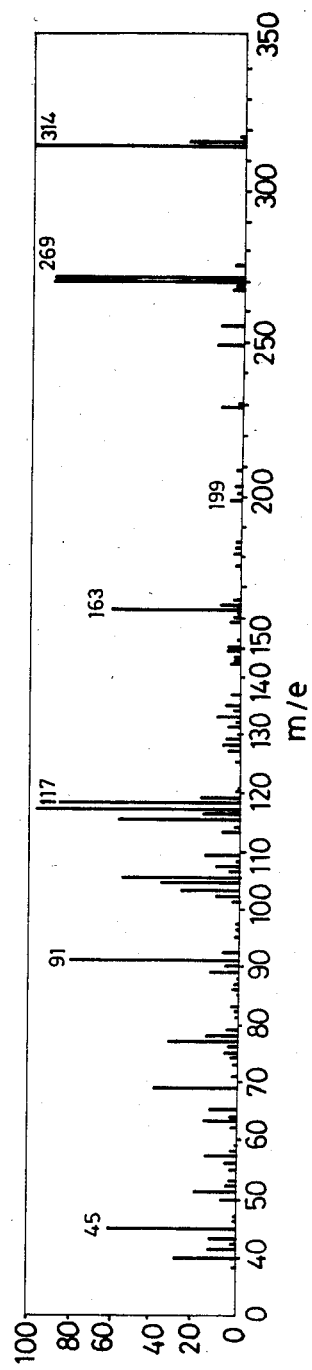

(2) Mass spectrum (at 20 eV); m/e=314; refer to FIG. 11

Figure 12:
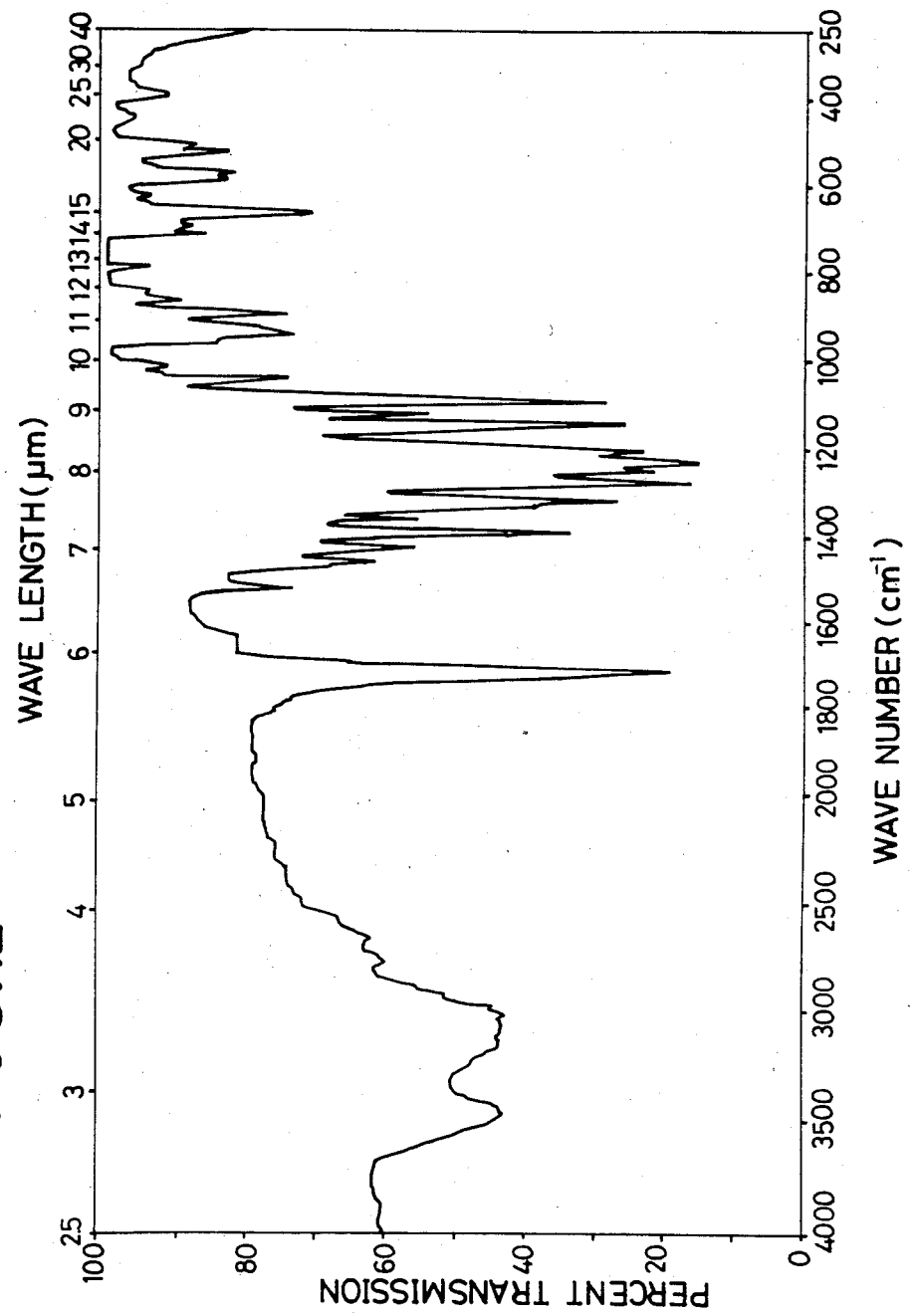

(3) Infrared absorption spectrum; shown in FIG. 12

Figure 13:
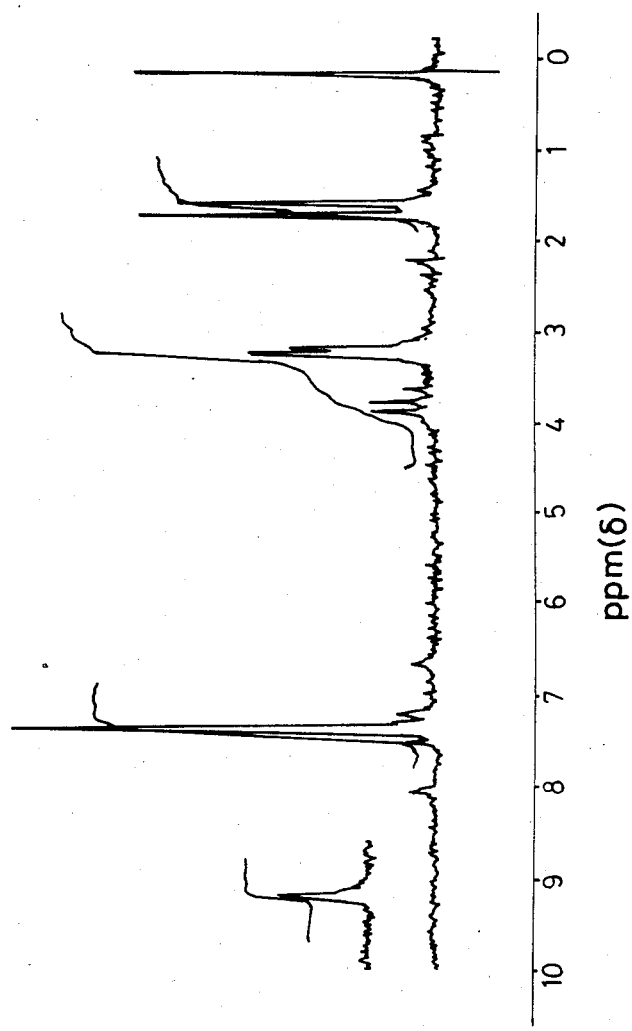

(4) $^1$H-NMR spectrum (at 60 MHz, in carbon tetrachloride and based on TMS); refer to FIG. 13;

δ12.0 ppm (s, 1H, —COO<u>H</u>);
6.9–7.5 (4H, Ar—<u>H</u>);
2.8–3.9 (4H,

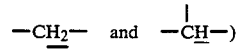

1.5 (d, 3H, —C<u>H</u>$_3$, J=7 Hz)

EXAMPLE 2

Synthesis of 2-[p-(2-methyl-3,3,3-trifluoropropyl)phenyl]propionic acid 2-1: Synthesis of the intermediate compound Into a 75 ml-three necked, round bottom flask provided with a mechanical stirrer and a dropping funnel, 75 ml of carbon disulfide was introduced and while stirring, 14.7 g (0.11 mol) of anhydrous aluminum chloride was added to be dispersed in carbon dissulfide. While cooling the flask from outside to keep the inner temperature at 0° to 5° C., 10.5 g (0.11mol) of propionyl chloride was dropped into the flask and then, while also keeping the inner temperature at 4° to 7° C., 18.8 g (0.1 mol) of 2- methyl-3,3,3-trifluoroprophylbenzene was added into the flask drop by drop during 2 hours. After 6 hours of stirring from the completion of the addition, the content of the flask was poured into a dilute hydrochloric acid in which ice blocks were floated. After spearating the layer of carbon disulfide, it was extracted with ether. The extract was washed with water, dried on calcium chloride and subjected to distillation to remove carbon disulfide to obtain 22.3 g of the reaction mixture as a pale brown liquid. On distilling the mixture, there was obtained 16.2 g of the fraction boiling at 85° to 86° C. under a reduced pressure of 2 mmHg. By analysing the fraction by gas chromatography, mass spectroscopy, $^1$H-NMR spectroscopy and infrared absorption spectroscopy, it was confirmed that the fraction was an isometric mixture of (2-methyl-3,3,3-trifluoropropyl)propiophenone containing at least 90% by weight of the para isomer (the intermediate compound).

2-2: Synthesis of the present compound 2-2-1 Preparation of thallium reagent

In a 300 ml-round bottomed flask, 64.7 g(0.61 mol) of methyl orthoformate and 48.8 g(1.53 mol) of methanol were mixed at room temperature, and 29.8 g (0.067 mol) of thallium nitrate trihydrate, Tl (NO$_3$)$_3$.3H$_2$O was dissolved in the mixture with the natural raise of the inner temperature from 15° to 18° C. By further adding 66 g of silica gel to the thus formed solution, the temperature of the solution was raised from 16° to 20° C. After stirring the solution for 10 minutes, the solvent was distilled off from the solution, and the residue was dried at 50° C. under a reduced pressure of 20 mmHg for 2 hours to obtain 95.5 g of white powder as the thallium reagent.

2-2-2 Oxidative rearrangement

In a 1 liter-round bottomed flask provided with a mechanical stirrer and a reflux condenser, 95.5 g of the thus prepared thallium reagent, 450 ml of carbon tetrachloride and 15 g (0.061 mol) of the intermediate compound synthesized in 2-1 were introduced to being into reaction under reflux condenser for 4 hours. After the reaction was over, the solid material in the reaction mixture was removed by filtration and the solvent was distilled off from the filtrate to obtain 14.0 g of a yellow liquid, from which 8.0 g of a fraction boiling at 85° to 89° C. under a reduced pressure of 2 mmHg was isolated by distillation.

2-2-3 Hydrolysis

Into 8.0 g of the fraction obtained in 2-2-2, 70 ml of ethanol and 1.8 g of sodium hydroxide were added, and the mixture was heated under a reflux condenser for 3 hours. After the reaction was over, the solvent was distilled off from the reaction mixture, and the residue was mixed with 100 ml of water, and then the mixture was washed 2 times with each 100 ml of ether. On adding a dilute hydrochloric acid to the aqueous phase to acidify, a precipitate appeared in the aqueous phase. After extracting the precipitate with ether, the ether was distilled off to obtain 4.9 g of a solid matter. Recrystallizing from n-hexane, the purified crystals were obtained, which were identified as 2-[p-(2-methyl-3,3,3-trifluoropropyl)phenyl]propionic acid by the following analyses.

Figure 8:
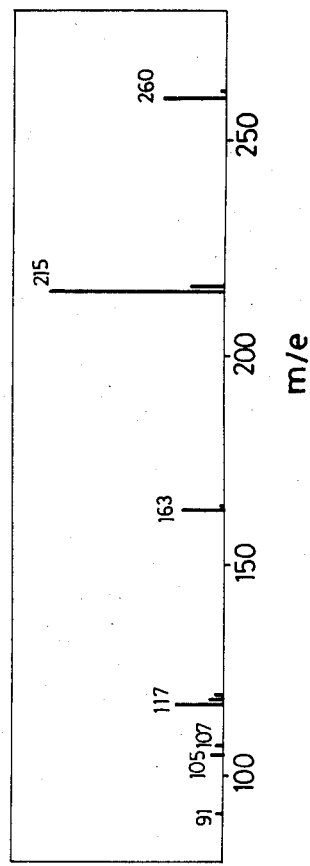

(1) Melting point; 53°-55° C. (2) Mass spectrum (at 20 eV); m/e=260; refer to FIG. 8

Figure 9:
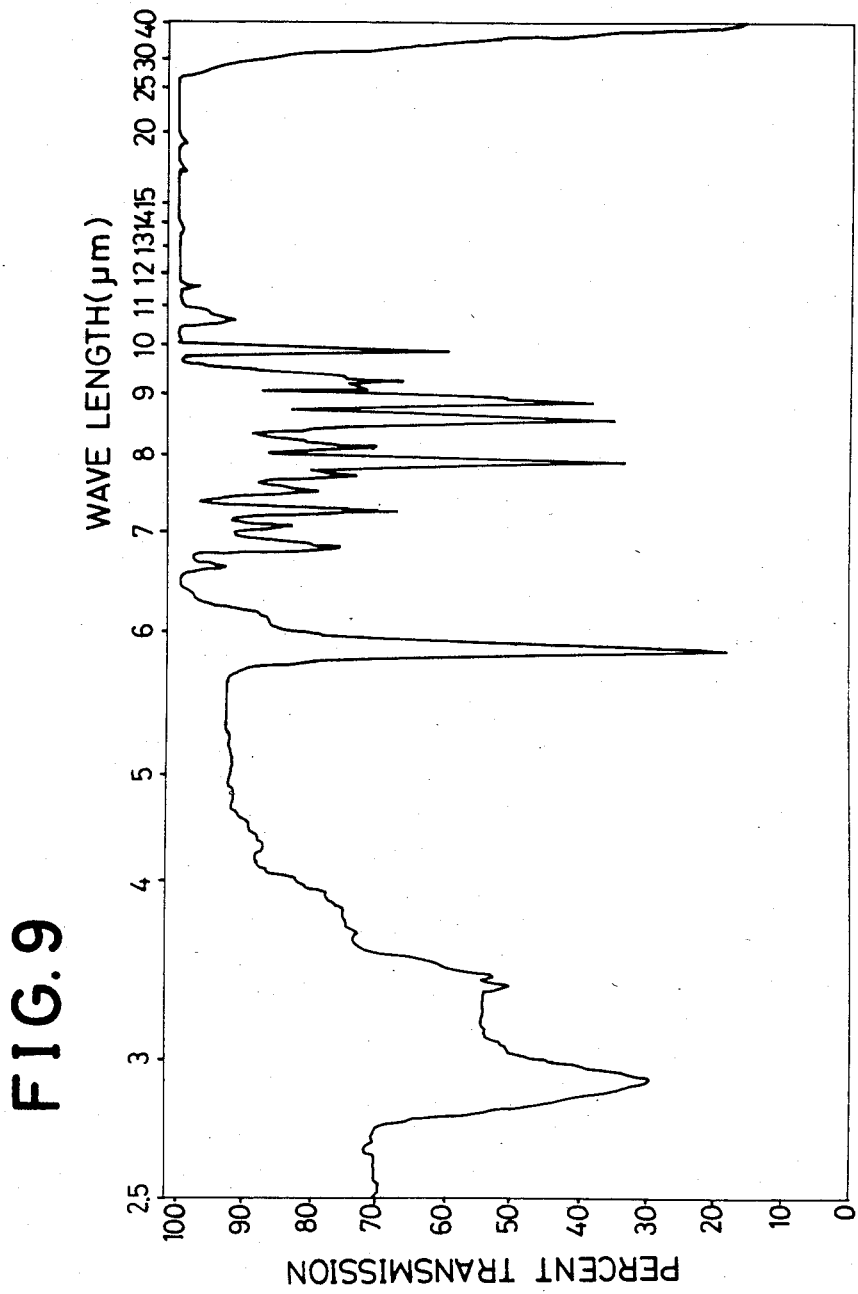

(3) Infrared absorption spectrum; shown in FIG. 9

(4) $^1$H-NMR spectrum (at 60 MHz, in carbon tetrachloride and based on TMS);

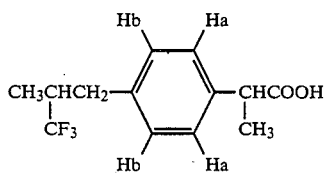

δ13.57 ppm (s, 1H:—COOH);
7.25 (d, 2H: Ha, J=8 Hz);
7.05 (d, 2H: Hb, J=8 Hz);
2.1-3.9 (m, 4H:

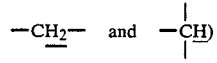

148 (d, 3H:

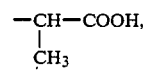

J=7 Hz);
1.02 (d, 3H:

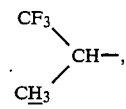

Figure 10:
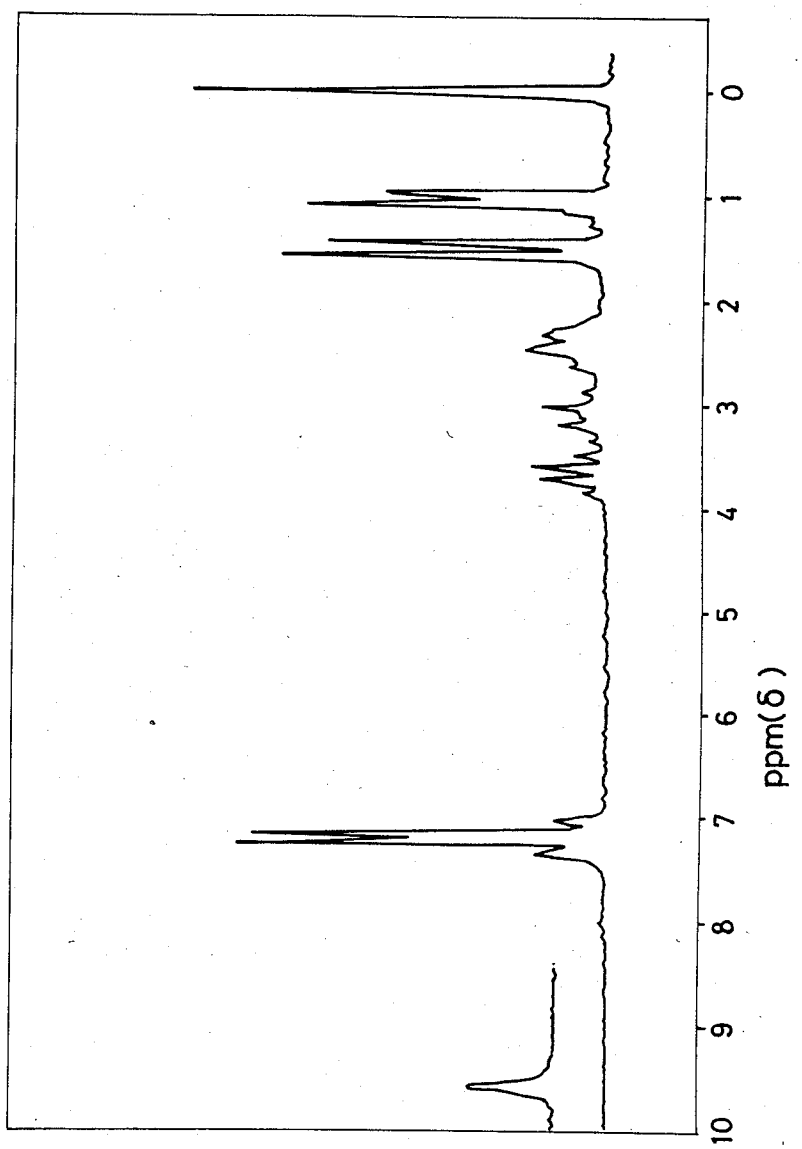

J=6Hz);
refer to FIG. 10

EXAMPLE 3

Synthesis of 2-[p-(3,3,3-trifluoropropyl)phenyl]propionic acid 3-1 Synthesis of the intermediate compound Into a 2 liter-round bottomed flask provided with a mechanical stirrer and a dropping funnel, 500 ml of carbon disulfide was introduced and while stirring, 110 g (0.825 mol) of anhydrous aluminum chloride was added to be suspended in carbon disulfide. While cooling the flask from outside to keep the temperature of the content of the flask (referred to as the inner temperature) at 0° to 5° C., 76.3 g (0.825 mol) of propionyl chloride was dropped into the flask during 50 minutes, and then, while also cooling the flask to keep the inner temperature at 0° to 5° C., 130.5 g (0.75 mol) of 3,3,3-trifluoropropylbenzene was added into the flask drop by drop. After 5 hours of stirring from the completion of the addition, at the time when the evolution of hydrogen chloride came to an end, the content of the flask was poured into a dilute hydrochloric acid in which ice blocks were floated. After separating the layer of carbon disulfide, it was washed with water, an aqueous 10% solution of sodium carbonate and then water, dried on calcium chloride and subjected to distillation to remove carbon disulfide to obtain 159.3 of the reaction mixture. On distilling the mixture, there was obtained 90.5 g of the fraction boiling at 100° to 104° C. under a reduced pressure of 1.8 mmHg. Recrystallizing the fraction from n-hexane, 72.5 g of a crystalline compound was obtained, which was identified as p-(3,3,3-trifluoropropyl)propiophenone by the following analyses:

(1) Melting point; 36.5°-37.5° C.;

(2) Mass spectrum (at 20 eV); m/e=230; refer to FIG. 1

Figure 2:
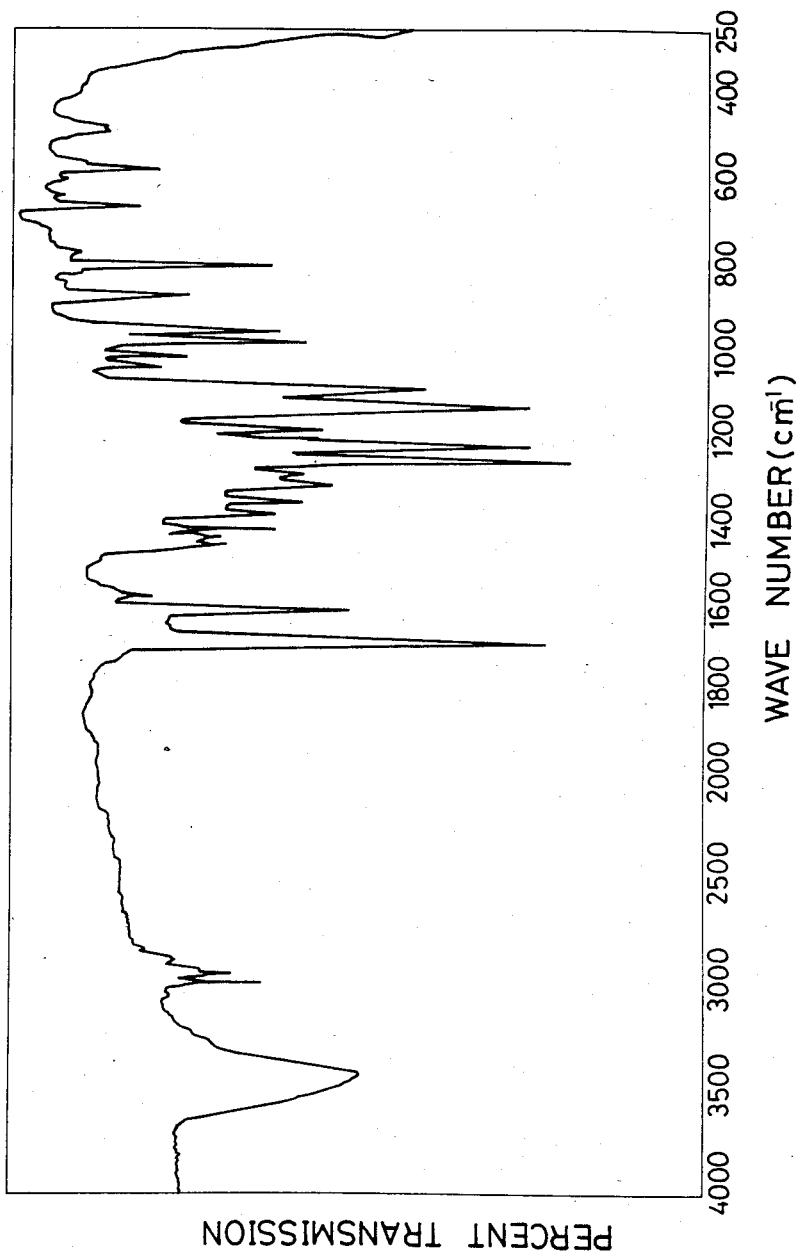

(3) Infrared absorption spectrum; shown in FIG. 2

Figure 3:
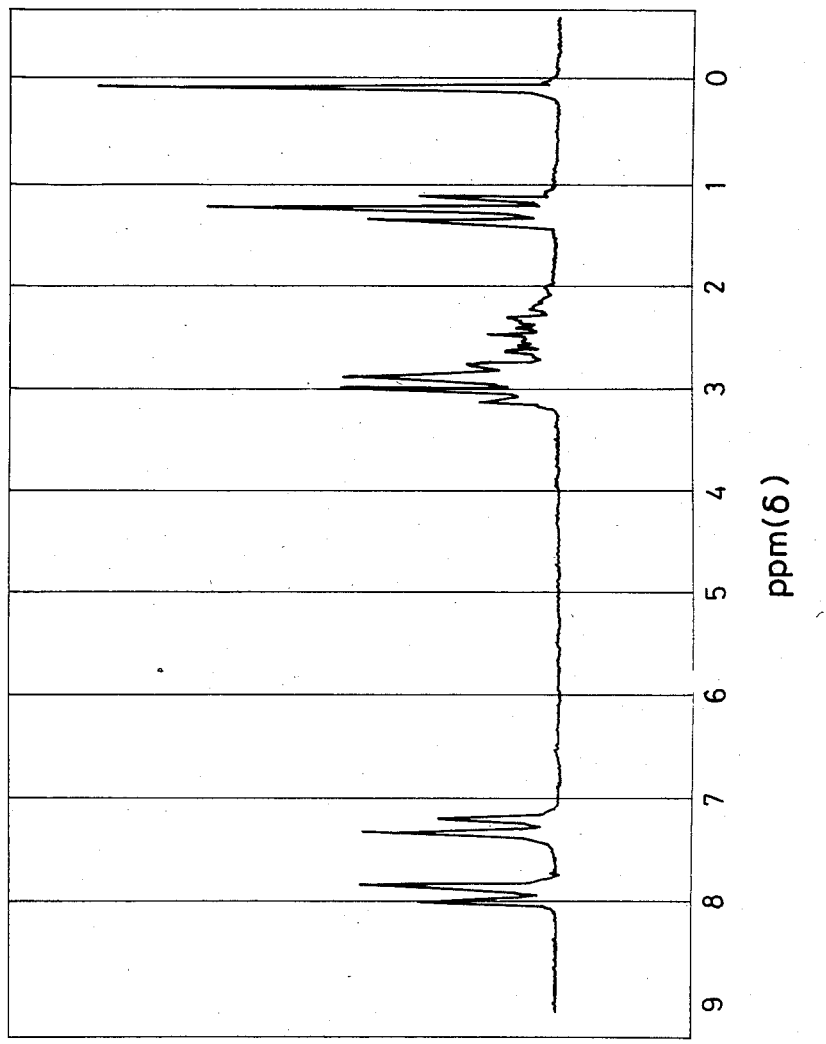

(4) $^1$H-NMR spectrum (at 60 MHz, in carbon tetrachloride and based on TMS);

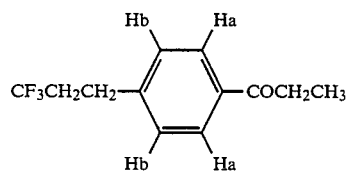

δ7.83 ppm (d, 2H: Ar—Ha, J=8 Hz);
7.20 (d, 2H: Ar—Hb, J=8 Hz);
2.87 (q, 2H: Ar—COCH$_2$—, J=8 Hz);
1.9–3.1 (m, 4H: —CH$_2$CH$_2$CF$_3$);
1.17 (t, 3H: —CH$_3$, J=7 Hz);
refer to FIG. 3

3-2 Synthesis of the present compound:
3-2-1 Preparation of thallium reagent

In a 500 ml-round bottomed flask, 160 ml of methyl orthoformate and 130 ml of methanol were mixed at room temperature, and 63.5 g (0.143 mol) of thallium nitrate trihydrate, Tl (NO$_3$)$_3$.3H$_2$O was dissolved in the mixture with the natural raise of temperature of the mixture from 14.5° to 23.5° C. By further adding 140 g of silica gel to the thus formed solution, the temperature of the solution was raised to 32° C. After cooling the solution for 10 minutes, the solvent was distilled off from the solution, and the residue was dried at 50° under a reduced pressure of 20 mmHg to obtain 196 g of white powder as the thallium reagent.

3-2-2 Oxidative rearrangement

In a 2 liter-round bottomed flask provided with a mechanical stirrer and a reflux condenser, 196 g of the thus prepared thallium reagent, 900 ml of carbon tetrachloride and 30 g (0.13 mol) of the intermediate compound synthesized in 3-1 were introduced to bring into reaction under reflux condenser for 4 hours. After the reaction was over, the solid material in the reaction mixture was removed by filtration and the solvent was distilled off from the filtrate to obtain 32.8 g of a yellow liquid.

The composition of the thus obtained liquid was examined by gas chromatography and gas chromatographic mass spectroscopy to be as follows;

| Composition of the product | |
|---|---|
| Component | Content (% by weight)* |
| CF$_3$CH$_2$CH$_2$—⟨Ph⟩—COCH$_2$CH$_3$ (unreacted intermediate compound) | 17.6 |
| CF$_3$CH$_2$CH$_2$—⟨Ph⟩—CH(CH$_3$)—COOCH$_3$ (Methyl ester of the present compound) | 73.9 |
| Others | 8.5 |

Figure 4:
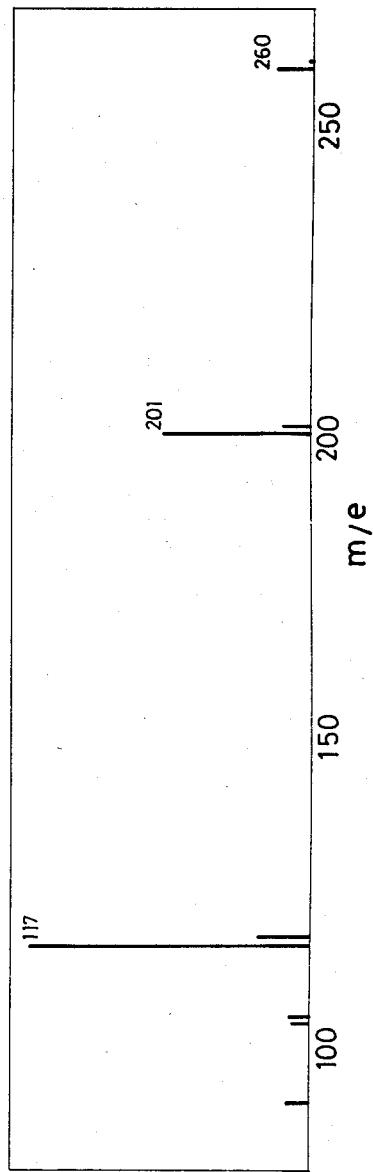

*Detemined by the comparison of the areas of the respective peaks appearing in the gas chromatogram A mass spectrogram of the thus synthesized methyl ester of the present compound taken at 20 eV is shown in FIG. 4.

3-2-3 Hydrolysis

Into 32.8 g of the yellow liquid obtained in 3-2-2, 190 ml of ethanol and 7.7 g of sodium hydroxide were added, and the mixture was heated under a reflux condenser for 2 hours. After the reaction was over, the solvent was distilled off from the reaction mixture, and the residue was mixed with 200 ml of water, and then the mixture was washed 2 times with each 200 ml of ether. On adding a dilute hydrochloric acid to the aqueous phase to acidify, a precipitate appeared in the aqueous phase. After extracting the precipitate with ether, the ether was distilled off to obtain 17 g of a solid matter. Recrystallizing from n-hexane, the purified crystals were obtained, which were identified at 2-[p-(3,3,3-trifluoropropyl)phenyl]propionic acid by the following analyses.

Figure 5:
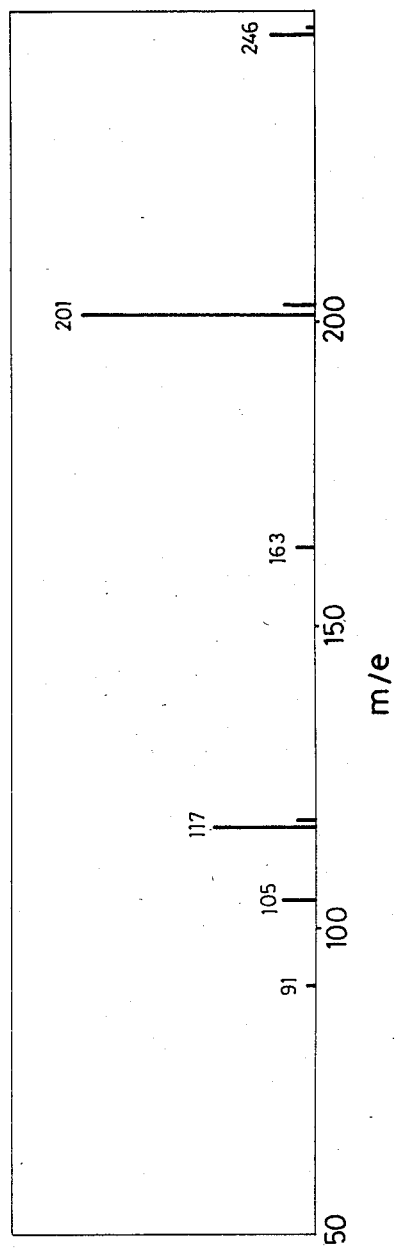
Figure 6:
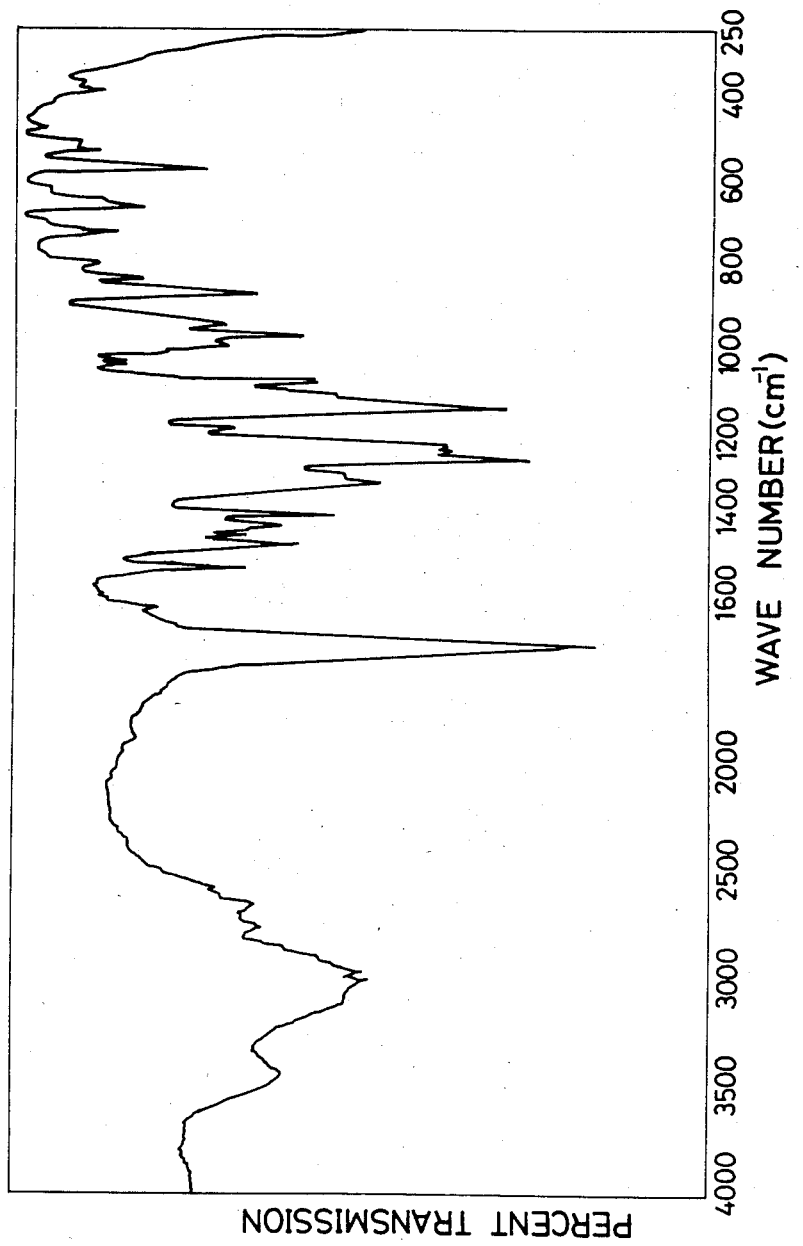

(1) Melting point; 75°–76.5° C.
(2) Mass spectrum (at 20 eV); m/e=246; refer to FIG. 5
(3) Infrared absorption spectrum; shown in FIG. 6
(4) $^1$H-NMR spectrum (at 60 MHz, in carbon tetrachloride and based on TMS);

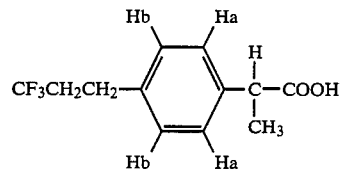

δ12.2 ppm (s, 1H: —COOH);
7.28 (d, 2H: Ar—Ha, J=8 Hz);
7.10 (d, 2H: Ar—Hb, J=8 Hz);
3.66 (q, 1H:

Figure 7:
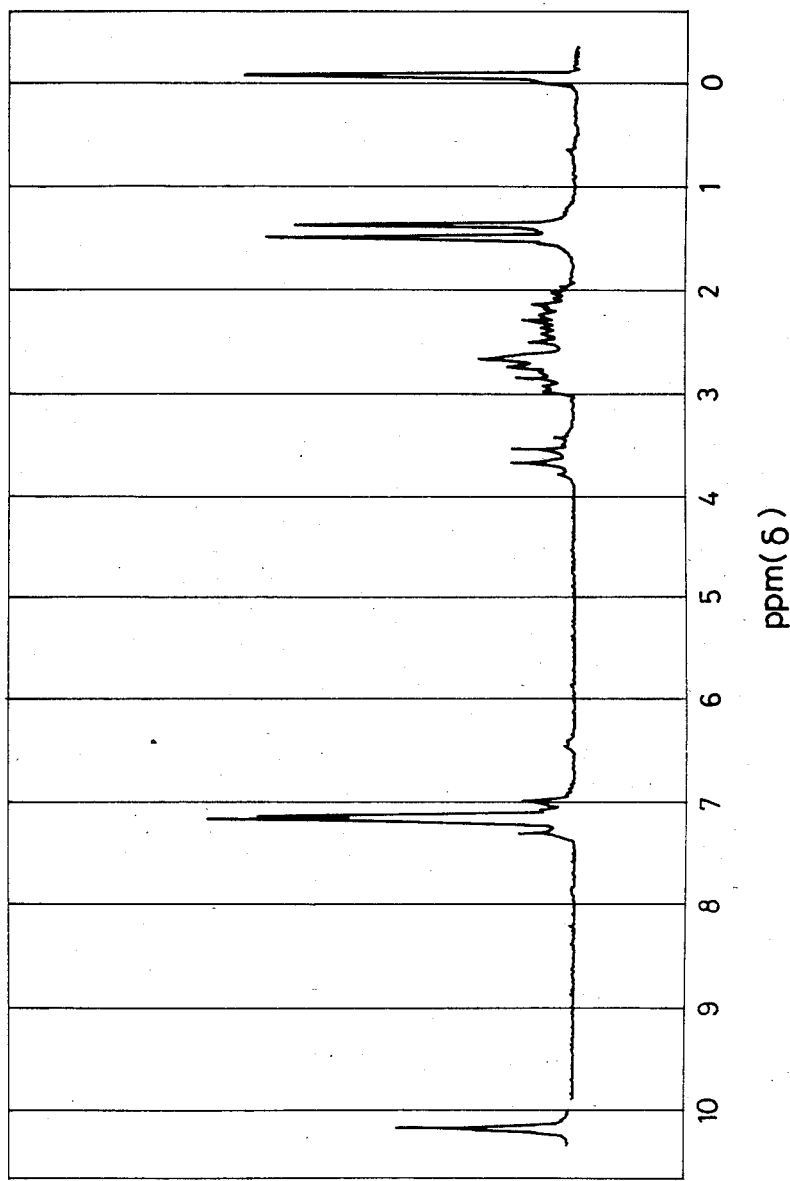

J=7 Hz);
1.88-3.05 (m, 4H: —CH$_2$CH$_2$CF$_3$); 1.48 (d, 3H: —CH$_3$, J=7 Hz);
refer to FIG. 7

TOXICOLOGICAL AND PHARMACOLOGICAL ACTIVITIES OF THE PRESENT COMPOUNDS

The specimens used in the following Examples are shown below.

Specimen I;
2-[p-(2-trifluoromethyl-3,3,3-trifluropropyl)phenyl]propionic acid of the present compound II;
2-[p-(2-methyl-3,3,3,-trifluropropyl)phenyl]propionic acid of the present compound III; 2-[p-(3,3,3-trifluropropyl)phenyl]propionic acid of the present compound IV; Ibprofen-- 2-(p-isobutylphenyl)propionic acid--as the comparative compound V; Aspirin-- acetyl salicyclic acid-- as the comparative compound

EXAMPLE 4

Acute toxicity of the present compound were determined as follows.

Each of the specimens was dispersed in an olive oil. The dispersion was administered to an ICR-JCL mouse orally by a stomach sonde at a predetermined amount. After administration, the intoxication symptoms were continuously observed for 14 days. $LD_{50}$ value was obtained from the cumulative mortality of the mice by applying the data to the Litchfield-Wilcoxon's graphical method.

The results are shown in Table 1.

TABLE 1

| Specimen | $LD_{50}$ (mg/Kg) |
|---|---|
| I | 1100 |
| II | 1040 |
| III | 1000 |
| IV | 1000 |

EXAMPLE 5

Mutagenicity of the present compound was examined by using 6 strains according to the Ames's method.

The strains used in this test were as follows.

*Salmonella typhimurium*; TA-98, TA-100, TA-1535, TA-1537, TA-1538

*Escherichia coli*; WP2 uvrA

The present compounds showed no mutagenicity.

EXAMPLE 6

Anti-inflammatory activity of the present compound was examined by using 10 female Wister rats of 110 to 130 g of body weight as one group following the method of C. A. Winter [refer to Proc. Soc. Exp. Biol. Med., 111, 544(1962)]in which the ratio of inhibiting the carrageenin-induced edema is determined.

An aqueous suspension of each specimen in an aqueous 1% carboxymethoxycellulose solution was orally administered to the rat in volume of 1 ml per 100 g body weight. The rat as the control group was administered with only an aqueous 1% solution of carboxymethoxycellulose. One hour after the administration, 0.1 ml of an aqueous 1% solution of carrageenin in physiological saline was injected into the plantar tissue of the right hind paw of the rat. Then, after 4 hours from the injection, the volume of the injected foot was measured to find the volume of swelling by subtracting the volume of foot before the injection from that value.

By comparing the volume of the swelling of the administered group to that of the control group, the ratio of inhibiting the swelling (I.R., %) was calculated according to the following formula:

$$I.R.\ (\%) = \left(1 - \frac{T}{C}\right) \times 100$$

wherein T represents the average volume of swelling in the group administered with the specimen, and C represents the average volume of swelling in the control group.

The results are shown in Table 2.

As seen from Table 2, the present compounds have anti-inflammatory activity higher than that of the conventional anti-inflammatory medicine (Ibprofen).

TABLE 2

| Oral Dose (mg/Kg) | Inhibition of carrageenin-induced edema (%) | | |
|---|---|---|---|
| | I | II | IV |
| 200 | 63 | 65 | 52 |
| 100 | 57 | 54 | 42 |
| 50 | 55 | 50 | 40 |
| 25 | 50 | | 29 |
| 10 | 46 | 40 | |
| 5. | 40 | 37 | |
| 2.5 | 37 | | |

EXAMPLE 7

Anti-inflammatory activity of the present compound was examined in the same manner as Example 6, except using female Wister rats of 92 to 112 g of body weight.

The results are shown in Table 3.

As seen from Table 3, the anti-inflammatory activity of the present compound is also higher than that of the conventional anti-inflammatory medicine (Aspirin).

TABLE 3

| Oral Dose (mg/kg) | Inhibition of carrageenin-induced edema (%) | |
|---|---|---|
| | III | V |
| 100 | 44 | 28 |
| 25 | 38 | 10 |

MANUFACTURE OF THE PHARMACETUICAL PREPARATIONS

Example 8

Capsule

A capsule was prepared by the following composition;

| the present compound | 10 parts by weight |
|---|---|
| heavy magnesium oxide | 15 |
| lactose | 75 |

The components mentioned above were mixed and pulverized followed by sifting to be powdery or granular material. By capsuling the material in capsules, the capsular preparation was obtained.

Granule

A granule was prepared by the following composition;

| the present compound | 45 parts by weight |
|---|---|
| starch | 15 |
| lactose | 16 |
| crystalline cellulose | 21 |
| polyvinyl alcohol | 3 |
| water | 30 |

The components mentioned above were uniformly mixed, kneaded, crushed, dried and subjected to sifting to obtain a granular preparation.

Tablet

To 96 parts by weight of the granular preparation obtained above, 4 parts by weight of calcium stearate was admixed, and the mixture was made into a tablet of 10 mm in diameter by the conventional method for tabletting.

Sugar-coated tablet

A sugar-coated tablet was prepared by the following composition;

| the present compound | 94 parts by weight |
|---|---|
| polyvinyl alcohol | 6 |
| water | 30 |

By using the components mentioned above, a granular preparation was prepared in the same manner as above. To 90 parts by weight of the granular preparation, 10 parts by weight of crystalline cellulose was admixed, and the mixture was made into a tablet of 8 mm in diameter by the conventional method for tabletting followed by coating the mixture of syrup, gelatin and precipitated calcium carbonate to obtain a sugar-coated tablet.

What is claimed is:

1. A compound represented by the general formula (I):

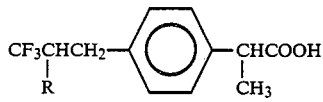 (I)

wherein R is a hydrogen atom, a methyl group or a trifluoromethyl group, or a salt thereof.

2. The compound of claim 1, which is 2-[p-(3,3,3-trifluoropropyl)phenyl]propionic acid, or a salt thereof.

3. The compound of claim 1, which is 2-[p-(2-methyl-3,3,3-trifluoropropyl)phenyl]propionic acid, or a salt thereof.

4. The compound of claim 1, which is 2-[p-(2-trifluoromethyl-3,3,3-trifluoropropyl)phenyl]propionic acid, or a salt thereof.

5. The compound of any one of claims 1 to 4, wherein the salt is a sodium of potassium salt.

6. A pharmaceutical composition in a dosage unit form comprising a compound represented by the general formula (I):

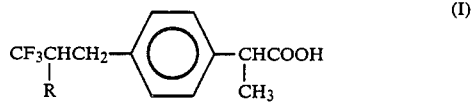 (I)

wherein R is a hydrogen atom, a methyl group or a trifluoromethyl group, or a salt thereof.

7. A method for treating inflammations in humans or animals comprising the step of administering to said animal or human an effective amount of the anti-inflammatory compound of the formula:

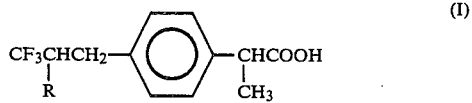 (I)

wherein R is a hydrogen atom, a methyl group, a trifluoromethyl group, or a salt thereof.

8. The method according to claim 7 wherein said compound is administered parenterally.

9. The method according to claim 7 wherein said compound is administered perorally.

10. The method according to claim 7 wherein said compound is 2-[p-(3,3,3-trifluoropropyl)phenyl]propionic acid, or a salt thereof.

11. The compound according to claim 7 wherein said compound is 2-[p-(2-methyl-3,3,3-trifluoropropyl)phenyl] propionic acid, or a salt thereof.

12. The compound according to claim 7 wherein said compound is 2-[p-(2-trifluoromethyl-3,3,3-trifluoropropyl) phenyl] propionic acid, or a salt thereof.

* * * * *

UNITED STATES PATENT AND TRADEMARK OFFICE
CERTIFICATE OF CORRECTION

PATENT NO. : 4,567,293

DATED : January 28, 1986

INVENTOR(S) : Kobyashi et al.

It is certified that error appears in the above-identified patent and that said Letters Patent is hereby corrected as shown below:

Column 1, line 18, change "propinonc" to --propionic--.

Column 2, line 19, change "$CF_3CHCH_2$" to --$CF_3CHCH_2$--.
                                                              F                    R Column 2, line 41, change "be perorally" to --be administered perorally--.

Column 2, line 44, change "carrier, adjuvant" to --carrier or adjuvant--.

Column 2, lines 59 and 60, change "indi-vidually" to --indi-viduality--.

Column 3, line 34, change "(2tri-" to --(2-tri---.

Column 4, line 14, change "developping" to --developing--.

Column 4, line 17, change "as it is" to --as it was--.

Column 4, line 51, change "dissulfide" to --disulfide--.

Column 4, line 56, change "trifluoroprophylbenzene" to --trifluoropropylbenzene--.

Column 4, line 61, change "spearating" to --separating--.

UNITED STATES PATENT AND TRADEMARK OFFICE
CERTIFICATE OF CORRECTION

PATENT NO. : 4,567,293

DATED : January 28, 1986

INVENTOR(S) : Kobayashi et al.

It is certified that error appears in the above-identified patent and that said Letters Patent is hereby corrected as shown below:

Column 7, line 22, change "raise" to --rise--.

Column 8, line 14, change "at" to --as--.

Column 8, line 67, change "were" to --was--.

Column 11, line 18, change "of" to --with--.

Column 12, line 2, change "of" to --or--.

Signed and Sealed this

Thirtieth Day of September 1986

[SEAL]

Attest:

DONALD J. QUIGG

Attesting Officer

Commissioner of Patents and Trademarks